(12) United States Patent
Cherchi et al.

(10) Patent No.: US 9,102,856 B2
(45) Date of Patent: Aug. 11, 2015

(54) PRE-SOAKING PROCESS FOR BIOMASS CONVERSION

(71) Applicant: Beta Renewables, S.p.A., Tortona (IT)

(72) Inventors: Francesco Cherchi, Novi Ligure (IT); Piero Ottonello, Genoa (IT); Simone Ferrero, Tortona (IT); Paolo Torre, Arenzano (IT); Danilo De Faveri, Novi Ligure (IT); Beatriz Rivas Torres, Arenzano (IT); Liliane Tonte Rensi, Tortona (IT); Daniele Riva, Prela' (IT); Federica Bosio, Adrara San Martino (IT)

(73) Assignee: Beta Renewables, S.p.A., Tortona (AL) (IT)

( * ) Notice: Subject to any disclaimer, the term of this patent is extended or adjusted under 35 U.S.C. 154(b) by 297 days.

(21) Appl. No.: 13/694,666

(22) Filed: Dec. 20, 2012

(65) Prior Publication Data

US 2013/0168602 A1 Jul. 4, 2013

(30) Foreign Application Priority Data

Dec. 28, 2011 (IT) .............................. TO2011A1219

(51) Int. Cl.
| | |
|---|---|
| *C07C 53/08* | (2006.01) |
| *C13K 13/00* | (2006.01) |
| *C09K 3/00* | (2006.01) |
| *C12P 19/02* | (2006.01) |
| *C13K 1/02* | (2006.01) |
| *D21C 1/02* | (2006.01) |
| *C13B 20/16* | (2011.01) |
| *D21C 5/00* | (2006.01) |

(52) U.S. Cl.
CPC . *C09K 3/00* (2013.01); *C07C 53/08* (2013.01); *C12P 19/02* (2013.01); *C13B 20/165* (2013.01); *C13K 1/02* (2013.01); *C13K 13/00* (2013.01); *C13K 13/007* (2013.01); *D21C 1/02* (2013.01); *C12P 2201/00* (2013.01); *D21C 5/005* (2013.01)

(58) Field of Classification Search
CPC ..... C12P 2201/00; C07C 51/47; C07C 53/08; C13B 20/165; D21C 1/102; C13K 13/00; C13K 13/007
See application file for complete search history.

(56) References Cited

U.S. PATENT DOCUMENTS

| | | | |
|---|---|---|---|
| 4,908,067 A | 3/1990 | Jack | |
| 2008/0057555 A1 | 3/2008 | Nguyen | |
| 2010/0041119 A1* | 2/2010 | Christensen et al. | ......... 435/162 |
| 2014/0234935 A1* | 8/2014 | Kusuda et al. | ................ 435/165 |
| 2015/0005484 A1* | 1/2015 | Kubo | ........................... 536/1.11 |

FOREIGN PATENT DOCUMENTS

| | | | |
|---|---|---|---|
| EP | 2172568 A1 | | 4/2010 |
| WO | WO2010/013129 | * | 2/2010 |

OTHER PUBLICATIONS

Search Report to Italian Priority Application No. TO2011A001219 dated Apr. 2, 2012.
Chinda, Evangalia; International Search Report; Apr. 26, 2013.
Chinda, Evangalia; Written Opinion of the International Search Authority; Apr. 26, 2013.

* cited by examiner

*Primary Examiner* — David M Brunsman
(74) *Attorney, Agent, or Firm* — Edwin A. Sisson, Attorney at Law, LLC (57) ABSTRACT

An improved method of conducting the pre-soaking step involving pre-soaking the ligno-cellulosic biomass in a liquid (water) at a temperature in the range of between 100° C. to 150° C. prior to soaking at higher temperatures. This material can then be soaked and soaked liquid filtered by nano-filtration. When nano-filtration is used, the pre-soak temperature can be in the range of 10° C. to 150° C.

9 Claims, 5 Drawing Sheets

PRE-SOAKING PROCESS FOR BIOMASS CONVERSION

PRIORITY AND CROSS REFERENCES

This patent application claims the priority from Italian Patent Application Number TO2011A001219 filed 28 Dec. 2011, the teachings of which are incorporated in their entirety.

BACKGROUND

WO201013129 is a patent application which is incorporated by reference in its entirety and teaches a process for the treatment of ligno-cellulosic biomass comprising the steps of: A) Soaking a ligno-cellulosic biomass feedstock in vapor or liquid water or mixture thereof in the temperature range of 100 to 210° C. for 1 minute to 24 hours to create a soaked biomass containing a dry content and a first liquid; B) Separating at least a portion of the first liquid from the soaked biomass to create a first liquid stream and a first solid stream; wherein the first solid stream comprises the soaked biomass; and C) Steam exploding the first solid stream to create a steam exploded stream comprising solids and a second liquid.

Claim 4 of WO201013129 teaches that the soaking step A can be preceded by a low temperature soaking step wherein the ligno-cellulosic biomass is soaked in liquid comprised of water at a temperature in the range of 25 to 100° C. for 1 minute to 24 hours and the low temperature soaking step is followed by a separation step to separate a least a portion of the liquid from the low temperature soak. It is even referred to a low temperature process.

What is not disclosed in WO201013129 is the further treatment of streams or the procedures disclosed in this instant application which further improve upon the steps and processes of WO201013129.

SUMMARY

This specification discloses a process for the treatment of ligno-cellulosic biomass, comprising the steps of
  A) Introducing a liquid stream comprised of water and a feedstream comprised of ligno-cellulosic biomass solids comprised of cellulose, sugars, into a pre-soaking vessel,
  B) Pre-soaking the feedstream with the liquid stream at a temperature in the range of greater than 100° C. to 150° C.,
  C) Separating at least a portion of liquid stream from the solids to create a first solids product stream and pre-soaked liquid product stream, and
  D) Soaking the first solids stream according to
    1) Soaking the solid product stream in vapor or liquid water or mixture thereof in the temperature range of 100° C. to 210° C. for 1 minute to 24 hours to create a second soaked biomass containing a dry content and a soaked liquid;
    2) Separating at least a portion of the soaked liquid from the second soaked biomass to create a soaked liquid stream and a second solid stream; wherein the second solid stream comprises the second soaked biomass.

It is further disclosed that the weight of sugars in the pre-soaked soaked liquid stream relative to the weight of the total sugars of the ligno-cellulosic biomass in the feedstream are less than a value selected from the group consisting of 5 weight %, 2.5 weight %, and 1 weight %.

It is also disclosed that the pre-soaking can be done for a time less than 48 hours.

A further step of filtering the soaked liquid stream can be done by nano-filtration.

It is further discloses that the soaked liquid have an instantaneous flux greater than 7 L/h-m$^2$, wherein the instantaneous flux is the flux when 72 L of a 190 L aliquot of the at least a portion of the soaked liquid have passed through a spiral nano-filter membrane conforming to the specifications that the membrane is a polyamide type thin film composite on polyester, has a magnesium sulfate rejection of greater than or equal to 98% when measured on 2000 ppm magnesium sulfate in water at 9 bar and 25° C. and having an outer diameter of 64.0 to 65.0 mm, a length of 432 mm and an inside diameter of 21 mm, the membrane having a cross-flow of 1.3-1.8 m3/h with a maximum pressure drop of 0.6 bar at 1 cP and design membrane area of 0.7 m$^2$.

It is further disclosed that the spiral nano-filter membrane conforms to a 2011 filter specification of NF99, available from Alfa Laval, (Sweden) or that the spiral nano-filter membrane actually be NF99, available from Alfa Laval, (Sweden) as provided by Alfa Laval in 2011.

It is also disclosed that the separation of at least a portion of the acetic acid is done by nano-filtration.

It is further disclosed, that when nano filtration is used or that flux is present, the following process may be used with all the above disclosed variations.
  A) Introducing a liquid stream comprised of water and a feedstream comprised of ligno-cellulosic biomass solids comprised of cellulose, glucans and xylans, into a pre-soaking vessel,
  B) Pre-soaking the feedstream with the liquid stream at a temperature in the range of 10° C. to 150° C.,
  C) Separating at least a portion of liquid stream from the solids to create a first solids product stream and a pre-soaked liquid product stream, and
  D) Treating the first solids stream with a soaking step comprising the steps of
  1) Soaking the first solids stream in vapor or liquid water or mixture thereof in the temperature range of 100° C. to 210° C. to create a second soaked biomass containing a dry content and a soaked liquid;
  2) Separating at least a portion of the soaked liquid from the second soaked biomass to create a soaked liquid stream comprised of suspended solids, monomeric sugar, oligomeric sugars, acetic acid, and furfural and a second solid stream; wherein the second solid stream comprises the second soaked biomass,
  E) Separating at least a portion of the soaked liquid from the suspended solids of the soaked liquid stream comprising monomeric sugars, oligomeric sugars, acetic acid, and furfural,
  F) Filtering at least a portion of the acetic acid from the at least a portion of the soaked liquid to create a permeate and a retentate.

DESCRIPTION

This specification is based upon the discovery that the maximum temperature of a first pre-soaking step prior to the pre-treatment of soaking which may or may not be followed by steam explosion, is the temperature at which the hemi-cellulose in the ligno-cellulosic biomass solubilizes. This temperature is highly variable and depends upon the type of ligno-cellulosic biomass for the amount of time the ligno-cellulosic biomass is kept at that temperature.

WO201013129 teaches a pre-soaking step, but teaches that the low temperature of first pre-soaking step should be between 25 and 100° C. This teaches away from higher temperatures greater than 100° C. Temperatures greater than 100° C. require pressure vessels, special heating kits, insulation and increases the capital and operating cost of the process.

It has also been discovered that after soaking below the solubility temperature of the hemi-cellulose the filterability of the removed liquid is greatly enhanced as measured by increased filter life. The pre-soaking step at the higher temperature removes critical filter plugging compounds, such that the purification step of the liquid after the soaking hydrolysis step need only use one unit operation such as one filter (e.g. nano-filtration as opposed to two unit operations in a series, (e.g. ultra-filtration followed by nanofiltrations). The process may have a centrifuge and/or bag filter of 1 micron size or greater prior to the nano-filtration, but the expensive ultra filtration is avoided and the process can be operated void of ultra-filtration.

Therefore one improvement over WO201013129 is that the pre-soaking does not have to be at a low temperature, but rather can be in the temperature range between 100° C. and 150° C., which does not include 100° C., the upper limit of WO201013129.

It has been learned that higher temperatures work better for removing the contaminants, particularly the contaminants which inhibit nano-filtration of the liquid from the soaking (not the pre-soaking) step.

The ligno-cellulosic biomass useful for this process can be characterized as follows. First, being apart from starch, the three major constituents in plant biomass are cellulose, hemi-cellulose and lignin, which are commonly referred to by the generic term ligno-cellulose. Polysaccharide-containing biomasses as a generic term include both starch and ligno-cellulosic biomasses. Therefore, some types of feedstocks can be plant biomass, polysaccharide containing biomass, and ligno-cellulosic biomass.

Polysaccharide-containing biomasses according to the present invention include any material containing polymeric sugars e.g. in the form of starch as well as refined starch, cellulose and hemi-cellulose.

Relevant types of biomasses for deriving the claimed invention may include biomasses derived from agricultural crops selected from the group consisting of starch containing grains, refined starch; corn stover, bagasse, straw e.g. from rice, wheat, rye, oat, barley, rape, sorghum; softwood e.g. *Pinus sylvestris, Pinus radiate*; hardwood e.g. *Salix* spp. *Eucalyptus* spp.; tubers e.g. beet, potato; cereals from e.g. rice, wheat, rye, oat, barley, rape, sorghum and corn; waste paper, fiber fractions from biogas processing, manure, residues from oil palm processing, municipal solid waste or the like. Although the experiments are limited to a few examples of the enumerated list above, the invention is believed applicable to all because the characterization is primarily to the unique characteristics of the lignin and surface area.

The ligno-cellulosic biomass feedstock used in the process is preferably from the family usually called grasses. The proper name is the family known as Poaceae or Gramineae in the Class Liliopsida (the monocots) of the flowering plants. Plants of this family are usually called grasses, or, to distinguish them from other graminoids, true grasses.

Bamboo is also included. There are about 600 genera and some 9,000-10,000 or more species of grasses (Kew Index of World Grass Species).

Poaceae includes the staple food grains and cereal crops grown around the world, lawn and forage grasses, and bamboo. Poaceae generally have hollow stems called culms, which are plugged (solid) at intervals called nodes, the points along the culm at which leaves arise. Grass leaves are usually alternate, *distichous* (in one plane) or rarely spiral, and parallel-veined. Each leaf is differentiated into a lower sheath which hugs the stem for a distance and a blade with margins usually entire. The leaf blades of many grasses are hardened with silica phytoliths, which helps discourage grazing animals. In some grasses (such as sword grass) this makes the edges of the grass blades sharp enough to cut human skin. A membranous appendage or fringe of hairs, called the ligule, lies at the junction between sheath and blade, preventing water or insects from penetrating into the sheath.

Grass blades grow at the base of the blade and not from elongated stem tips. This low growth point evolved in response to grazing animals and allows grasses to be grazed or mown regularly without severe damage to the plant.

Flowers of Poaceae are characteristically arranged in spikelets, each spikelet having one or more florets (the spikelets are further grouped into panicles or spikes). A spikelet consists of two (or sometimes fewer) bracts at the base, called glumes, followed by one or more florets. A floret consists of the flower surrounded by two bracts called the lemma (the external one) and the palea (the internal). The flowers are usually hermaphroditic (maize, monoecious, is an exception) and pollination is almost always anemophilous. The perianth is reduced to two scales, called lodicules, that expand and contract to spread the lemma and palea; these are generally interpreted to be modified sepals.

The fruit of Poaceae is a caryopsis in which the seed coat is fused to the fruit wall and thus, not separable from it (as in a maize kernel).

There are three general classifications of growth habit present in grasses; bunch-type (also called caespitose), stoloniferous and rhizomatous.

The success of the grasses lies in part in their morphology and growth processes, and in part in their physiological diversity. Most of the grasses divide into two physiological groups, using the C3 and C4 photosynthetic pathways for carbon fixation. The C4 grasses have a photosynthetic pathway linked to specialized Kranz leaf anatomy that particularly adapts them to hot climates and an atmosphere low in carbon dioxide.

C3 grasses are referred to as "cool season grasses" while C4 plants are considered "warm season grasses". Grasses may be either annual or perennial. Examples of annual cool season are wheat, rye, annual bluegrass (annual meadowgrass, *Poa annua* and oat). Examples of perennial cool season are orchard grass (cocksfoot, *Dactylis glomerata*), fescue (*Festuca* spp), Kentucky Bluegrass and perennial ryegrass (*Lolium perenne*). Examples of annual warm season are corn, sudangrass and pearl millet. Examples of Perennial Warm Season are big bluestem, indiangrass, bermuda grass and switch grass.

One classification of the grass family recognizes twelve subfamilies: These are 1) anomochlooideae, a small lineage of broad-leaved grasses that includes two genera (*Anomochloa, Streptochaeta*); 2) Pharoideae, a small lineage of grasses that includes three genera, including *Pharus* and *Leptaspis*; 3) Puelioideae a small lineage that includes the African genus *Puelia*; 4) Pooideae which includes wheat, barley, oats, brome-grass (Bronnus) and reed-grasses (*Calamagrostis*); 5) Bambusoideae which includes bamboo; 6) Ehrhartoideae, which includes rice, and wild rice; 7) Arundinoideae, which includes the giant reed and common reed 8) Centothecoideae, a small subfamily of 11 genera that is sometimes included in Panicoideae; 9) Chloridoideae including the lovegrasses (*Eragrostis*, ca. 350 species, including *teff*), dropseeds (*Sporobolus, some* 160 species), finger millet (*Eleusine coracana* (L.) Gaertn.), and the muhly grasses (*Muhlenbergia*, ca. 175 species); 10) Panicoideae including panic grass, maize, sorghum, sugar cane, most millets, fonio and bluestem grasses. 11) Micrairoideae; 12) Danthoniodieae including pampas grass; with *Poa* which is a genus of about 500 species of grasses, native to the temperate regions of both hemispheres.

Agricultural grasses grown for their edible seeds are called cereals. Three common cereals are rice, wheat and maize (corn). Of all crops, 70% are grasses.

Sugarcane is the major source of sugar production. Grasses are used for construction. Scaffolding made from bamboo is able to withstand typhoon force winds that would break steel scaffolding.

Larger bamboos and *Arundo donax* have stout culms that can be used in a manner similar to timber, and grass roots stabilize the sod of sod houses. *Arundo* is used to make reeds for woodwind instruments, and bamboo is used for innumerable implements.

Therefore a preferred ligno-cellulosic biomass may be selected from the group consisting of the grasses and woods. A preferred ligno-cellulosic biomass may be selected from the group consisting of the plants belonging to the conifers, angiosperms, Poaceae and/or Gramineae families. Another preferred ligno-cellulosic biomass may also be that biomass having at least 10% by weight of it dry matter as cellulose, or more preferably at least 5% by weight of its dry matter as cellulose.

The ligno-cellulosic biomass will also comprise carbohydrate(s) selected from the group of carbohydrates based upon the glucose, xylose, and mannose monomers. Being derived from ligno-cellulosic biomass, means that the ligno-cellulosic biomass of the feed stream will comprise glucans and xylans and lignin.

The ligno-cellulosic biomass feedstock may also be from woody plants. A woody plant is a plant that uses wood as its structural tissue. These are typically perennial plants whose stems and larger roots are reinforced with wood produced adjacent to the vascular tissues. The main stem, larger branches, and roots of these plants are usually covered by a layer of thickened bark. Woody plants are usually either trees, shrubs, or lianas. Wood is a structural cellular adaptation that allows woody plants to grow from above ground stems year after year, thus making some woody plants the largest and tallest plants.

These plants need a vascular system to move water and nutrients from the roots to the leaves (xylem) and to move sugars from the leaves to the rest of the plant (phloem). There are two kinds of xylem: primary that is formed during primary growth from procambium and secondary xylem that is formed during secondary growth from vascular cambium. What is usually called "wood" is the secondary xylem of such plants.

The two main groups in which secondary xylem can be found are:
1) conifers (Coniferae): there are some six hundred species of conifers. All species have secondary xylem, which is relatively uniform in structure throughout this group. Many conifers become tall trees: the secondary xylem of such trees is marketed as softwood.
2. angiosperms (Angiospermae): there are some quarter of a million to four hundred thousand species of angiosperms. Within this group secondary xylem has not been found in the monocots (e.g Poaceae). Many non-monocot angiosperms become trees, and the secondary xylem of these is marketed as hardwood.

The term softwood is used to describe wood from trees that belong to gymnosperms. The gymnosperms are plants with naked seeds not enclosed in an ovary. These seed "fruits" are considered more primitive than hardwoods. Softwood trees are usually evergreen, bear cones, and have needles or scale-like leaves. They include conifer species e.g. pine, spruces, firs, and cedars. Wood hardness varies among the conifer species.

The term hardwood is used to describe wood from trees that belong to angiosperm family. Angiosperms are plants with ovules enclosed for protection in an ovary. When fertilized, these ovules develop into seeds. The hardwood trees are usually broad-leaved; in temperate and boreal latitudes they are mostly deciduous, but in tropics and subtropics mostly evergreen. These leaves can be either simple (single blades) or they can be compound with leaflets attached to a leaf stem. Although variable in shape all hardwood leaves have a distinct network of fine veins. The hardwood plants include e.g. Aspen, Birch, Cherry, Maple, Oak and Teak.

Glucans include the monomers, dimers, oligomers and polymers of glucan in the ligno-cellulosic biomass. Of particular interest is 1,4 beta glucan which is particular to cellulose, as opposed to 1,4 alpha glucan. The amount of 1,4 beta glucan(s) present in the pre-treated ligno-cellulosic biomass should be at least 5% by weight of the pre-treated ligno-cellulosic biomass on a dry basis, more preferably at least 10% by weight of the pre-treated ligno-cellulosic biomass on a dry basis, and most preferably at least 15% by weight of the pre-treated ligno-cellulosic biomass on a dry basis.

Xylans include the monomers, dimers, oligomers and polymers of xylan in the pre-treated ligno-cellulosic biomass composition.

While the pre-treated ligno-cellulosic biomass can be free of starch, substantially free of starch, or have a starch content of 0 weight percent, or be void of starch. Starch, if present, can be less than 75% by weight of the dry content. There is no preferred starch range as its presence is not believed to affect the hydrolysis to glucose. Ranges for the starch amount, if present, are between 0 and 75% by weight of the dry content, 0 to 50% by weight of the dry content, 0 to 30% by weight of the dry content and 0 to 25% by weight of the dry content.

Because this invention is to hydrolysis of glucose, the specification and inventors believe that any ligno-cellulosic biomass with 1,4 beta glucans can be used as a feed stock for this improved hydrolysis process.

The pre-treatment used on the ligno-cellulosic biomass can be any pre-treatment known in the art and those to be invented in the future.

The pre-treatment used to pre-treat the pre-treated ligno-ceullosic biomass is used to ensure that the structure of the ligno-cellulosic content is rendered more accessible to the catalysts, such as enzymes, and at the same time the concentrations of harmful inhibitory by-products such as acetic acid, furfural and hydroxymethyl furfural remain substantially low.

The current strategies of pre-treatment are subjecting the ligno-cellulosic material to temperatures between 110-250° C. for 1-60 min e.g.:

Hot Water Extraction

Multistage dilute acid hydrolysis, which removes dissolved material before inhibitory substances are formed Dilute acid hydrolysis at relatively low severity conditions Alkaline wet oxidation Steam explosion Almost any pre-treatment with subsequent detoxification If a hydrothermal pre-treatment is chosen, the following conditions are preferred:

Pre-treatment temperature: 110-250° C., preferably 120-240° C., more preferably 130-230° C., more preferably 140-220° C., more preferably 150-210° C., more preferably 160-200° C., even more preferably 170-200° C. or most preferably 180-200° C.

Pre-treatment time: 1-60 min, preferably 2-55 min, more preferably 3-50 min, more preferably 4-45 min, more preferably 5-40 min, more preferably 5-35 min, more preferably 5-30 min, more preferably 5-25 min, more preferably 5-20 min and most preferably 5-15 min.

Dry matter content after pre-treatment is preferably at least 20% (w/w). Other preferable higher limits are contemplated as the amount of biomass to water in the pre-treated ligno-cellulosic feedstock be in the ratio ranges of 1:4 to 9:1; 1.3.9 to 9:1, 1:3.5 to 9:1, 1:3.25 to 9:1, 1:3 to 9:1, 1:2.9 to 9:1, 1:2 to 9:1, 1.15 to 9:1, 1:1 to 9:1, and 1:0.9 to 9:1.

Polysaccharide-containing biomasses according to the present invention include any material containing polymeric sugars e.g. in the form of starch as well as refined starch, cellulose and hemi-cellulose. However, as discussed earlier, the starch is not a primary component.

A preferred pre-treatment process is the two step soak/extract followed by steam explosion as described below.

A preferred pretreatment of a ligno-cellulosic biomass include a soaking of the ligno-cellulosic biomass feedstock and a steam explosion of at least a part of the soaked ligno-cellulosic biomass feedstock.

The soaking occurs in a substance such as water in either vapor form, steam, or liquid form or liquid and steam together, to produce a product.

The product is a soaked biomass containing a soaking liquid, with the soaking liquid usually being water in its liquid or vapor form or some mixture.

This soaking can be done by any number of techniques that expose a substance to water, which could be steam or liquid or mixture of steam and water, or, more in general, to water at high temperature and high pressure. The temperature should be in one of the following ranges: 145 to 165° C., 120 to 210° C., 140 to 210° C., 150 to 200° C., 155 to 185° C., 160 to 180° C. Although the time could be lengthy, such as up to but less than 24 hours, or less than 16 hours, or less than 12 hours, or less than 9 hours or less than 6 hours; the time of exposure is preferably quite short, ranging from 1 minute to 6 hours, from 1 minute to 4 hours, from 1 minute to 3 hours, from 1 minute to 2.5 hours, more preferably 5 minutes to 1.5 hours, 5 minutes to 1 hour, 15 minutes to 1 hour.

If steam is used, it is preferably saturated, but could be superheated. The soaking step can be batch or continuous, with or without stirring. A low temperature soak prior to the high temperature soak can be used. The temperature of the low temperature soak is in the range of 25 to 90° C. Although the time could be lengthy, such as up to but less than 24 hours, or less than 16 hours, or less than 12 hours, or less than 9 hours or less than 6 hours; the time of exposure is preferably quite short, ranging from 1 minute to 6 hours, from 1 minute to 4 hours, from 1 minute to 3 hours, from 1 minute to 2.5 hours, more preferably 5 minutes to 1.5 hours, 5 minutes to 1 hour, 15 minutes to 1 hour.

Either soaking step could also include the addition of other compounds, e.g. $H_2SO_4$, $NH_3$, in order to achieve higher performance later on in the process.

The product comprising the soaking liquid, or soaked liquid, is then passed to a separation step where the at least a portion of the soaking liquid is separated from the soaked biomass. The liquid will not completely separate so that at least a portion of the soaking liquid is separated, with preferably as much soaking liquid as possible in an economic time frame. The liquid from this separation step is known as the soaked liquid stream comprising the soaking liquid. The soaked liquid will be the liquid used in the soaking, generally water and the soluble species of the feedstock. These water soluble species are glucan, xylan, galactan, arabinan, glucooligomers, xylooligomers, galactoligomers and arabinoligomers. The solid biomass is called the first solid stream as it contains most, if not all, of the solids.

The separation of the soaked liquid can again be done by known techniques and likely some which have yet been invented. A preferred piece of equipment is a press, as a press will generate a liquid under high pressure.

The first solid stream may then optionally be steam exploded to create a steam exploded stream, comprising solids. Steam explosion is a well known technique in the biomass field and any of the systems available today and in the future are believed suitable for this step. The severity of the steam explosion is known in the literature as Ro, and is a function of time and temperature and is expressed as $$Ro = t \exp[(T-100)/14.75]$$

with temperature, T expressed in Celsius and time, t, expressed in minutes.

The formula is also expressed as Log(Ro), namely $$\mathrm{Log}(Ro) = \mathrm{Ln}(t) + [(T-100)/14.75].$$

Log(Ro) is preferably in the ranges of 2.8 to 5.3, 3 to 5.3, 3 to 5.0 and 3 to 4.3.

The steam exploded stream may be optionally washed at least with water and there may be other additives used as well. It is conceivable that another liquid may used in the future, so water is not believed to be absolutely essential. At this point, water is the preferred liquid. The liquid effluent from the optional wash is the third liquid stream. This wash step is not considered essential and is optional.

The washed exploded stream is then processed to remove at least a portion of the liquid in the washed exploded material. This separation step is also optional. The term at least a portion is removed, is to remind one that while removal of as much liquid as possible is desirable (preferably by pressing), it is unlikely that 100% removal is possible. In any event, 100% removal of the water is not desirable since water is needed for the subsequent hydrolysis reaction. The preferred process for this step is again a press, but other known techniques and those not invented yet are believed to be suitable. The products separated from this process are solids in the second solid stream and liquids in the second liquid stream.

One aspect of the invention involves exposing the ligno-cellulosic biomass to a pre-soaking step before a soaking step in a temperature range of between 100° C. and 150° C., where between means that the temperature of 100° C. and 150° C. are not included. The temperature range of 105° C. to 150° C., which includes 105° C. and 150° C. is also a preferred range. A temperature in the range of 110° C. to 150° C. is also a preferred range. Also contemplated is a temperature range of between 100° C. and 145° C. The temperature range of 105° C. to 145° C., which includes 105° C. and 145° C. is also a preferred range. A temperature in the range of 110° C. to 145° C. is also a preferred range.

The pre-soaking time could be lengthy, such as up to but preferably less than 48 hours, or less than 24 hours, or less than 16 hours, or less than hours, or less than 9 hours or less than 6 hours; the time of exposure is preferably quite short, ranging from 1 minute to 6 hours, from 1 minute to 4 hours, from 1 minute to 3 hours, from 1 minute to 2.5 hours, more preferably 5 minutes to 1.5 hours, 5 minutes to 1 hour, 15 minutes to 1 hour.

The pre-soaking step is done in the presence of a liquid which is the pre-soaked liquid. After soaking, this liquid preferably has removed less than 5% by weight of the total sugars in the raw material, more preferably, less than 2.5% by weight of the total sugars in the raw material being more preferable, with less than 1% by weight of the total sugars in the raw material, being the most preferred.

This pre-soaking step is useful as a modification to the soaking step of a biomass pre-treatment step. In soaking (not pre-soaking) of the biomass pre-treatment steps, the soaked liquid which has been separated from the soaked solids will preferably have reduced filter plugging components so that the soaked liquid can be easily nano-filtered. A property of the soaked liquid is that it should have an instantaneous flux greater than 7 L/h-m$^2$, wherein the instantaneous flux is the flux when 72 L of a 190 L aliquot of the at least a portion of the soaked liquid have passed through a spiral nano-filter membrane conforming to the specifications that the membrane is a polyamide type thin film composite on polyester, has a magnesium sulfate rejection of greater than or equal to 98% when measured on 2000 ppm magnesium sulfate in water at 9 bar and 25° C. and having an outer diameter of 64.0 to 65.0 mm, a length of 432 mm and an inside diameter of 21 mm, the membrane having a cross-flow of 1.3-1.8 m3/h with a maximum pressure drop of 0.6 bar at 1 cP and design membrane area of 0.7 m$^2$.

While having an instantaneous flux of greater than 7 is preferred, the instantaneous flux, according to method described, can be greater than a value selected from a group consisting of 7, 8, 9, 10, and 15.

When paired with the nano-filtration step, the pre-soaking temperature can be expanded to the range of 10° C. to 150° C., 25° C. to 150° C. even more preferable, with 25° C. to 145° C. even more preferable, and 25° C. to 100° C. and 25° C. to 90° C. also being preferred ranges.

EXPERIMENTS

A comparison between three experiments is presented.
Raw material is wheat straw in all experiments.
Compositions were classified in terms of water soluble components (WS) and water insoluble components (WIS), with the individual breakdown in Table 1—Component Listing

TABLE 1

| Component Listing | |
|---|---|
| Water Soluble Components (WS) | |
| soluble sugars | monomeric sugars (xylose, glucose) and oligomeric sugars (xylooligomers, glucooligomers) |

TABLE 1-continued

| Component Listing | |
|---|---|
| known soluble components | acetic acid, Hydroxymethylfurfural (HMF), furfural, salts, ashes |
| unknown soluble components | water soluble components different from soluble sugars and known soluble components |
| Water Insoluble Components WIS | |
| insoluble sugars | glucans, xylans |
| known insoluble components | insoluble acetyl groups |
| unknown insoluble components | all insoluble components different from insoluble sugars and known insoluble components |

WS components were classified as soluble sugars, known soluble components and unknown soluble components.

Soluble sugars means glucose, xylose, glucooligomers, xylooligomers

Known soluble components means components on the following list: acetic acid, Hydroxymethylfurfural (HMF), Furfural, salts, and ashes.

Unknown soluble components means all soluble components different from sugars and known soluble components.

WIS components were classified as insoluble sugars, known insoluble components and unknown insoluble components.

Insoluble sugars means glucans and xylans. Known insoluble components means insoluble acetyl groups.

Unknown insoluble components means all insoluble components different from insoluble sugars and known insoluble components.

Analytical measurements were performed according to the following NREL standards NREL Analytical Method
Determination of Structural Carbohydrates and Lignin in Biomass
Laboratory Analytical Procedure (LAP) Issue Date: Apr. 25, 2008
Technical Report NREL/TP-510-42618 Revised April 2008
Determination of Extractives in Biomass
Laboratory Analytical Procedure (LAP) Issue Date: Jul. 17, 2005
Technical Report NREL/TP-510-42619 January 2008

Preparation of Samples for Compositional Analysis

Laboratory Analytical Procedure (LAP) Issue Date: Sep. 28, 2005
Technical Report NREL/TP-510-42620 January 2008
Determination of Total Solids in Biomass and Total Dissolved Solids in Liquid Process Samples
Laboratory Analytical Procedure (LAP) Issue Date: Mar. 31, 2008
Technical Report NREL/TP-510-42621 Revised March 2008
Determination of Ash in Biomass
Laboratory Analytical Procedure (LAP) Issue Date: Jul. 17, 2005
Technical Report NREL/TP-510-42622 January 2008
Determination of Sugars, Byproducts, and Degradation Products in Liquid Fraction Process Samples
Laboratory Analytical Procedure (LAP) Issue Date: Dec. 8, 2006
Technical Report NREL/TP-510-42623 January 2008

Determination of Insoluble Solids in Pretreated Biomass Material

Laboratory Analytical Procedure (LAP) Issue Date: Mar. 21, 2008

NREL/TP-510-42627 March 2008

Experiment 1 (Control)

An amount of 23 Kg of raw material on dry basis was introduced in a continuous reactor and subjected to a soaking treatment at a temperature of 155° C. for 65 minutes. The soaked mixture was separated in a soaked liquid and a fraction containing the solid soaked raw material by means of a press. The fraction containing the solid soaked raw material was subjected to steam explosion at a temperature of 190° C. for a time of 4 minutes.

Steam exploded products were separated into a steam explosion liquid and a steam exploded solid.

Experiment 2

An amount of 22 Kg of raw material on dry basis was introduced in a continuous reactor with water at a ratio 1:3 and subjected to a presoaking treatment at the temperature of 130° C. for 30 minutes.

After presoaking, a presoaked liquid was separated from presoaked raw material by means of a press.

Presoaked raw material was subjected to soaking and steam explosion treatments as described in experiment 1.

Experiment 3

An amount of 22 Kg of raw material on dry basis was introduced in a batch reactor with water at a ratio 1:16 and subjected to a presoaking treatment at the temperature of 65° C. for 3 hours. The mixture was continuously agitated during pre-soaking.

After presoaking, a presoaked liquid was separated from presoaked raw material by means of a press.

Presoaked raw material was subjected to soaking and steam explosion treatments as described in experiment 1.

Results

Table 2 is the compositions of raw material (ligno-cellulosic biomass, e.g. wheat straw) of experiment 1, raw material, presoaked liquid and presoaked raw material of experiments 2 and 3.

|  | Experiment 1 | Experiment 2 | | | | Experiment 3 | | |
| --- | --- | --- | --- | --- | --- | --- | --- | --- |
|  | (control) raw material | raw material | presoaked raw material | pre-soaked liquid | volatile components | raw material | pre-soaked material | Pre-soaked liquid |
| WS (kg) | 1.75 | 1.45 | 1.17 | 0.32 | 0.68 | 1.63 | 0.28 | 2.46 |
| soluble sugars (kg) | 0.07 | 0.12 | 0.05 | 0.08 | 0.00 | 0.12 | 0.00 | 0.11 |
| known soluble components (kg) | 0.16 | 0.08 | 0.07 | 0.04 | 0.00 | 0.87 | 0.28 | 1.30 |
| unknown soluble components (kg) | 1.52 | 1.24 | 1.06 | 0.21 | 0.68 | 0.64 | 0.00 | 1.05 |
| WIS (kg) | 21.25 | 20.55 | 19.83 | 0.00 | 0.00 | 20.33 | 19.27 | 0.00 |
| insoluble sugars (kg) | 12.32 | 13.1 | 13.2 | 0.00 | 0.00 | 13.5 | 13.5 | 0.00 |
| known insoluble components (kg) | 0.36 | 0.4 | 0.3 | 0.00 | 0.00 | 0.5 | 0.5 | 0.00 |
| unknown insoluble components (kg) | 8.63 | 7.06 | 6.26 | 0.00 | 0.00 | 6.34 | 5.35 | 0.00 |
| | | presoaked liquid content | | | | | | |
| Percentage by weight of components removed from raw material | | | | 4.5% | | | | 11.2% |
| Weight of sugars removed relative to weight of the dry raw material | | | | 0.3% | | | | 0.5% |
| Weight of known solubles removed relative to weight of the dry raw material | | | | 0.2% | | | | 5.9% |
| Weight of unknown solubles removed relative to weight of the dry raw material | | | | 0.9% | | | | 4.8% |
| Weight of volatiles removed relative to weight of the dry raw material | | | | 3.1% | | | | 0.0% |
| Weight of sugars removed relative to weight of sugars in raw material | | | | 0.6% | | | | 0.8% |

Table 2 contains also the percentage content in presoaked liquid with respect to the raw material weight of sugars, other components, unknown components and volatile components. Table 2 contains also the percentage content of sugars in presoaked liquid with respect to the amount of sugars in raw material.

The presoaking of experiment 2 and experiment 3 removes 4.5% and 11.2% in weight of total weight of raw materials. In experiment 2, conducted at a higher temperature than experiment 3, also volatile components of 0.68 Kg of unknown product were present. Experiment 2 removes 0.3% of the weight of sugars contained in the raw material, corresponding to 0.6% of the weight of sugars contained in raw material. Experiment 3 removes 0.5% of the weight of sugars contained in the raw material, corresponding to 0.8% of the weight of sugars contained in raw material Table 3 contains the composition of soaked liquid after the soaking step of Experiments 1 to 3 including the percentage content on dry basis of known soluble components, unknown soluble components, insoluble components, acetic acid, monomeric sugars and oligomeric sugars. Acetic acid was inserted in the table separated from the known soluble components.

TABLE 3

SOAKING LIQUID COMPOSITION

|  | Experiment 1 (control) | Experiment 2 | Experiment 3 |
| --- | --- | --- | --- |
| known soluble components | 11.85% | 11.40% | 5.07% |
| unknown soluble components | 31.86% | 25.11% | 21.79% |
| insoluble components | 3.02% | 5.90% | 2.30% |
| acetic acid | 4.84% | 5.20% | 3.54% |
| monomeric sugars | 5.91% | 4.01% | 3.13% |
| oligomeric sugars | 42.51% | 48.38% | 64.17% |

Figure 1:
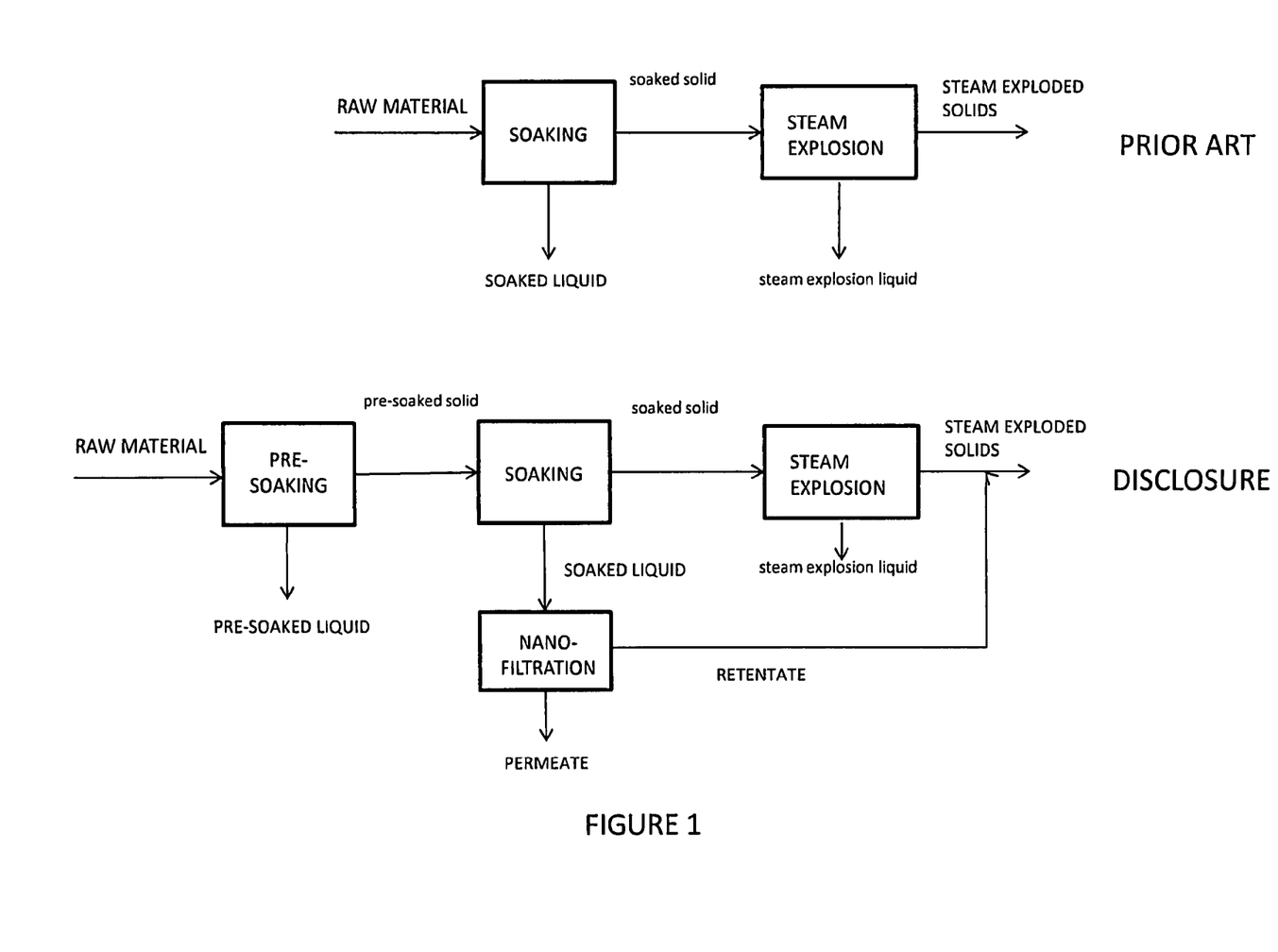
FIG. 1 has two schematics showing the prior art and an embodiment of the proposed process of the invention.
Figure 2:
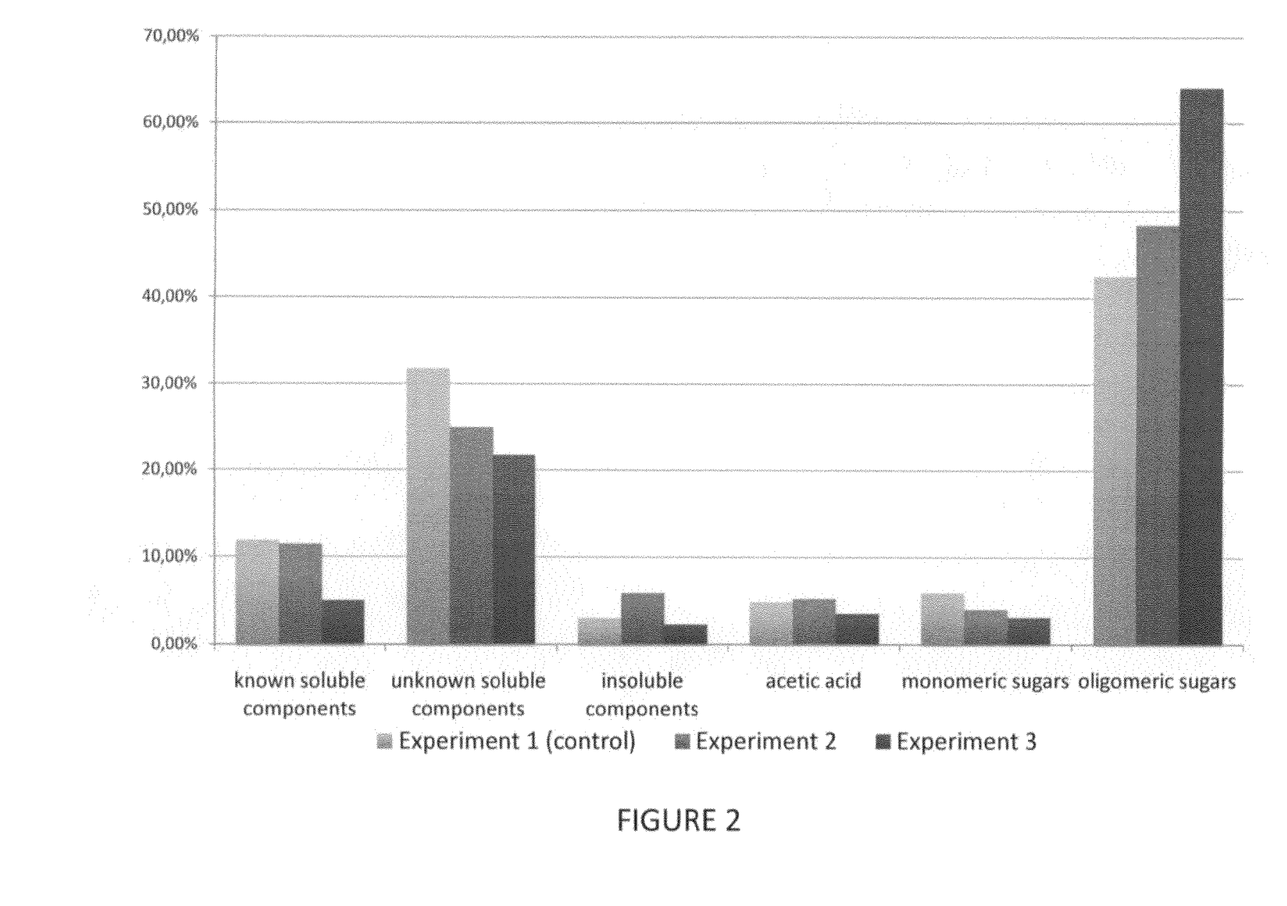
FIG. 2 shows the composition of the Soaked Liquid with and without the pre-soak step.

FIG. 2 contains a bar graph of the soaked liquid composition of experiments 1 to 3.

Table 4 contains the composition of steam exploded solids from Experiments 1 to 3 including the percentage content on dry basis of known soluble components, unknown soluble components, monomeric sugars and oligomeric sugars and insoluble sugars.

TABLE 4

STEAM EXPLODED SOLIDS COMPOSITION

|  | Experiment 1 (control) | Experiment 2 | Experiment 3 |
| --- | --- | --- | --- |
| Known soluble components | 4.60% | 3.53% | 4.43% |
| unknown insoluble components | 37.10% | 30.33% | 27.95% |
| monomeric sugars | 0.47% | 0.50% | 0.81% |
| oligomeric sugars | 5.19% | 7.44% | 10.40% |
| insoluble sugars | 52.63% | 58.19% | 56.41% |

Figure 3:
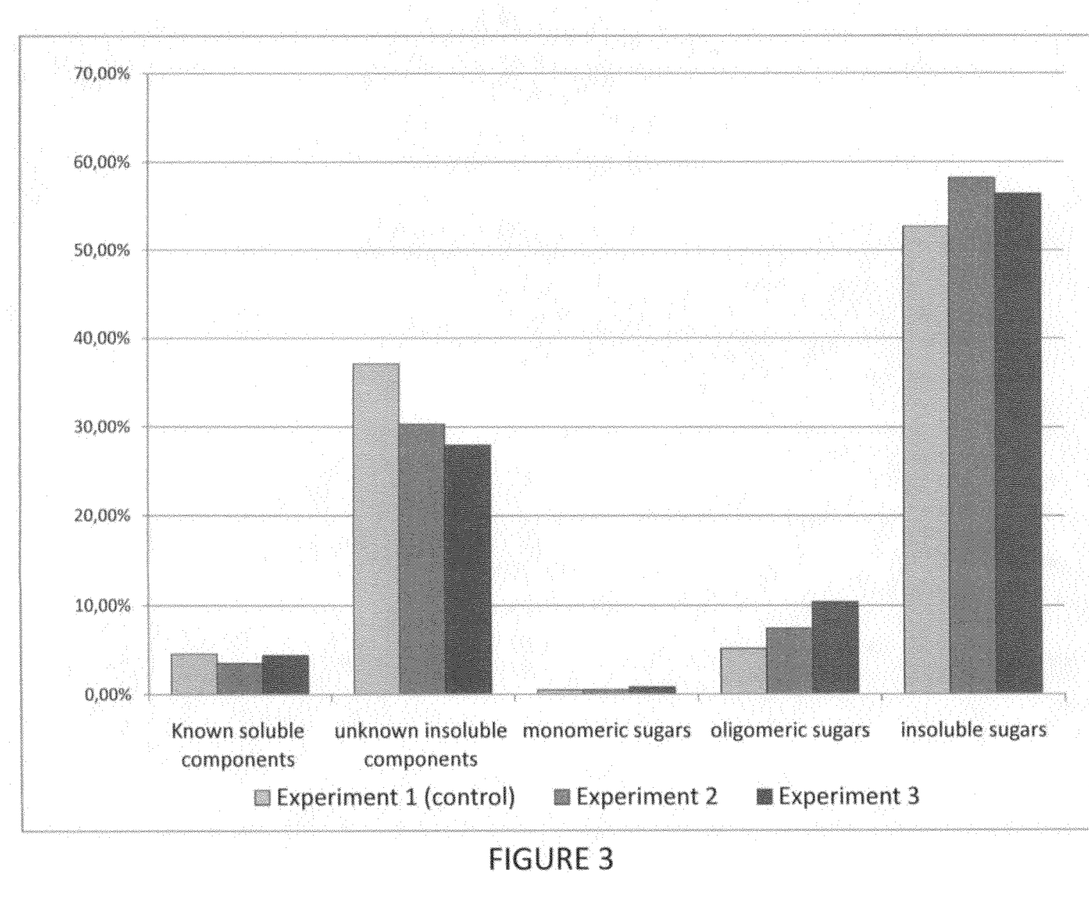
FIG. 3 shows the composition of the Steam Exploded Solids with and without the pre-soak step.

FIG. 3 contains a bar graph of the steam exploded solid composition of experiments 1 to 3.

Experiment 4

Experiment 4 was conducted for assessing the filterability of soaked liquids produced in experiments 1 to 3.

Soaked liquids were subjected to a preliminary pre-separation step to remove solids, by means of centrifugation and macro filtration (bag filter with filter size of 1 micron). Centrifugation was performed by means of a Alfa Laval CLARA 80 centrifuge at 8000 rpm.

Pre-separated liquids were subjected to nano-filtration by means of a Alfa Laval 2.5" equipment (membrane code NF99 2517/48), according to the following procedure.

Permeate flow stability was checked by means of flushing with de-mineral water, at room temperature (25° C.) and 4 bar. Flow rate of the permeate was measured. An amount of 192 liter of soaked liquid were inserted in the feed tank. Before test, the system was flushed for 5 minutes, without pressure, in order to remove the water.

The system was set at the operating conditions (pressure: 25-30 bar, temperature: 30-35° C.).

Retentate stream was recycled in the feed tank and permeate stream was dumped.

The test was run until the volume of liquid in the feed tank was reduced up to 62.5% of the initial soaked liquid volume, corresponding to 72 μliters of permeate and 120 liters of retentate.

Nanofiltered permeate and retentate were collected.

Figure 4:
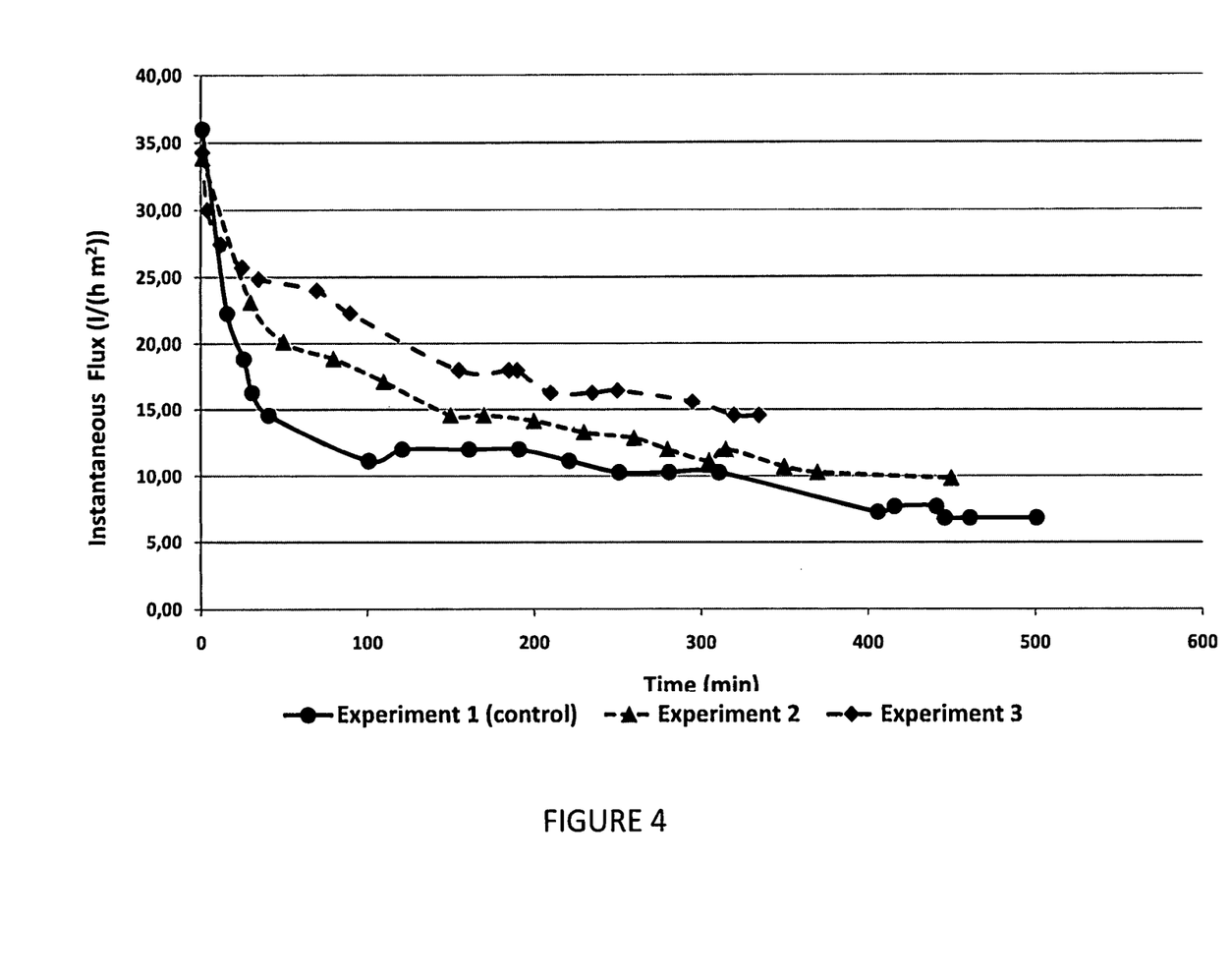
FIG. 4 shows the flux of the soaked liquid stream from each experiment as a function of time.

FIG. 4 contains the graph of instantaneous flux of the permeate from pre-separated soaked liquids across the nano-filtration system as a function of time. Soaked liquids from presoaked raw materials of experiments 2 and 3 have an instantaneous flux higher than soaked liquid from experiment 1 and the time needed for filtering a specific volume is reduced.

Figure 5:
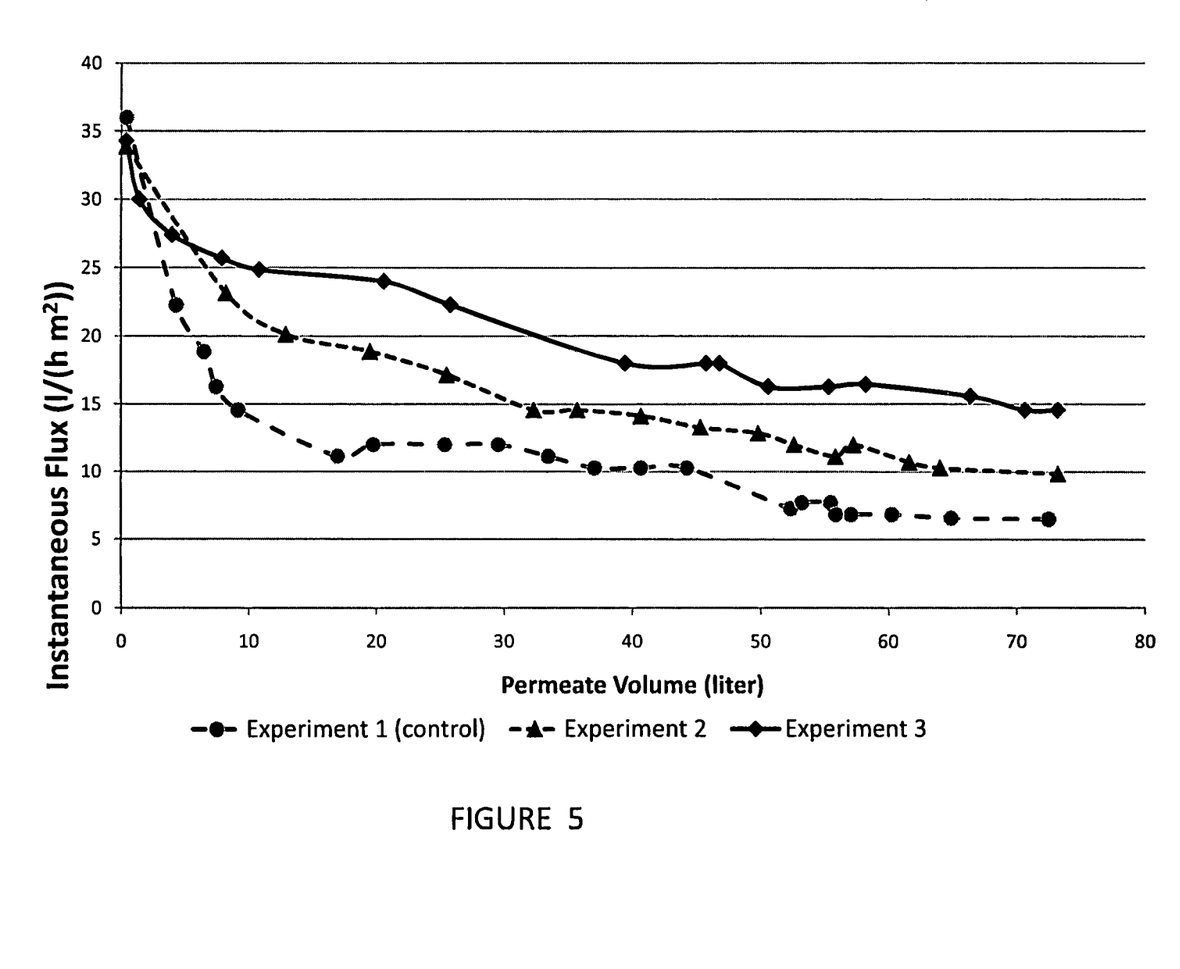
FIG. 5 shows the flux of the soaked liquid stream from each experiment expressed as a function of the volume of permeate passed through the filter.

FIG. 5 contains the graph of instantaneous flux of the permeate from pre-separated soaked liquids across the nano-filtration system as a function of the volume of permeate generated. Soaked liquids from presoaked raw materials of experiments 2 and 3 have an instantaneous flux higher than soaked liquid from experiment 1 and the time needed for filtering a specific volume is reduced.

The experiments highlight that by introducing a pre-soaking it is possible to filter a certain amount of liquid in a shorter time obtaining a higher flux. As a consequence, the complexity and costs of the filtration system needed in an industrial application are considerably reduced.

We claim:

1. A process for the treatment of ligno-cellulosic biomass, comprising the steps of
    A) Introducing a liquid stream comprised of water and a feedstream comprised of ligno-cellulosic biomass solids comprised of cellulose, and sugars into a pre-soaking vessel,
    B) Pre-soaking the feedstream with the liquid stream at a temperature in the range of greater than 100° C. to 150° C.,
    C) Separating at least a portion of liquid stream from the solids to create a first solids product stream and a pre-soaked liquid product stream, and
    D) Soaking the first solids stream according to
        1) Soaking the solid product stream in vapor or liquid water or mixture thereof in the temperature range of 100° C. to 210° C. for 1 minute to 24 hours to create a second soaked biomass containing a dry content and a soaked liquid;
        2) Separating at least a portion of the soaked liquid from the second soaked biomass to create a soaked liquid stream and a second solid stream; wherein the second solid stream comprises the second soaked biomass.

2. A process according to claim 1, wherein the weight of sugars in the pre-soaked liquid stream relative to weight of the sugars of the ligno-cellulosic biomass in the feedstream are less than 5 weight %.

3. The process according to claim 1, wherein the pre-soaking is done for a time less than 48 hours.

4. The process of claim 1, wherein the soaked liquid stream is filtered by nano-filtration.

5. The process according to claim 4, wherein the at least a portion of the soaked liquid has an instantaneous flux greater than 7 L/h-m$^2$, wherein the instantaneous flux is the flux when 72 L of a 190 L aliquot of the at least a portion of the soaked liquid have passed through a spiral nano-filter membrane conforming to the specifications that the membrane is a polyamide type thin film composite on polyester, has a magnesium sulfate rejection of greater than or equal to 98% when measured on 2000 ppm magnesium sulfate in water at 9 bar and 25° C. and having an outer diameter of 64.0 to 65.0 mm, a length of 432 mm and an inside diameter of 21 mm, the membrane having a cross-flow of 1.3-1.8 m3/h with a maximum pressure drop of 0.6 bar at 1 cP and design membrane area of 0.7 m$^2$.

6. A process for the treatment of ligno-cellulosic biomass, comprising the steps of
   A) Introducing a liquid stream comprised of water and a feedstream comprised of ligno-cellulosic biomass solids comprised of cellulose, and sugars into a pre-soaking vessel,
   B) Pre-soaking the feedstream with the liquid stream at a temperature in the range of 10° C. to 150° C.,
   C) Separating at least a portion of the liquid stream from the solids to create a first solids product stream and a pre-soaked liquid product stream, and
   D) Treating the first solids stream with a soaking step comprising the steps of
      1) Soaking the first solids stream in vapor or liquid water or mixture thereof in the temperature range of 100° C. to 210° C. to create a second soaked biomass containing a dry content and a soaked liquid;
      2) Separating at least a portion of the soaked liquid from the second soaked biomass to create a soaked liquid stream comprised of suspended solids, monomeric sugar, oligomeric sugars, acetic acid, and furfural and a second solid stream; wherein the second solid stream comprises the second soaked biomass,
   E) Separating at least a portion of the soaked liquid from the suspended solids of the soaked liquid stream comprising monomeric sugars, oligomeric sugars, acetic acid, and furfural,
   F) Filtering at least a portion of the acetic acid from the at least a portion of the soaked liquid to create a permeate and a retentate, wherein the filtering comprises a nano-filtration.

7. A process according to claim 6, wherein the weight of sugars in the pre-soaked liquid stream relative to weight of the sugars of the ligno-cellulosic biomass in the feedstream are less than 5 weight %.

8. The process according to claim 6, wherein the at least a portion of the soaked liquid has an instantaneous flux greater than 7 L/h-m$^2$, wherein the instantaneous flux is the flux when 72 L of a 190 L aliquot of the at least a portion of the soaked liquid have passed through a spiral nano-filter membrane conforming to the specifications that the membrane is a polyamide type thin film composite on polyester, has a magnesium sulfate rejection of greater than or equal to 98% when measured on 2000 ppm magnesium sulfate in water at 9 bar and 25° C. and having an outer diameter of 64.0 to 65.0 mm, a length of 432 mm and an inside diameter of 21 mm, the membrane having a cross-flow of 1.3-1.8 m3/h with a maximum pressure drop of 0.6 bar at 1 cP and design membrane area of 0.7 m$^2$.

9. The process of claim 6, wherein separation of at least a portion of the acetic acid is done by nanofiltration.

\* \* \* \* \*